(12) United States Patent
Buchmann et al.

(10) Patent No.: US 7,563,924 B2
(45) Date of Patent: Jul. 21, 2009

(54) 9-CHLORO-15-DEOXYPROSTAGLANDIN DERIVATIVES, PROCESS FOR THEIR PREPARATION AND THEIR USE AS MEDICAMENTS

(75) Inventors: Bernd Buchmann, Hohen Neuendorf (DE); Daryl Faulds, Mill Valley, CA (US); William Guilford, Belmont, CA (US); Gernot Langer, Berlin (DE); Judy Li, Emeryville, CA (US); Bernhard Lindenthal, Berlin (DE); Werner Skuballa, Berlin (DE); Luisella Toschi, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 143 days.

(21) Appl. No.: 11/602,690

(22) Filed: Nov. 20, 2006

(65) Prior Publication Data

US 2007/0203096 A1   Aug. 30, 2007

Related U.S. Application Data

(60) Provisional application No. 60/738,780, filed on Nov. 21, 2005.

(51) Int. Cl.
C07C 69/74 (2006.01)
A61K 31/557 (2006.01)

(52) U.S. Cl. .................. 560/121; 560/118; 562/500; 514/530; 514/573

(58) Field of Classification Search ............. 514/530, 514/573; 560/60, 61, 62, 118, 121; 562/500; 568/379
See application file for complete search history.

(56) References Cited

U.S. PATENT DOCUMENTS 4,444,788 A * 4/1984 Skuballa et al. ............. 514/247
6,110,969 A * 8/2000 Tani et al. .................. 514/530

FOREIGN PATENT DOCUMENTS

EP   1 306 087 A   5/2003

OTHER PUBLICATIONS

Abe, N. et al. Prostaglandin E2 and iL-4Provide naive CD4+T Cells with distinct inhibitory signals for the priming of INF-γ Production, Oct. 1997, Cellular Immunilogy, vol. 181, iss. 1, pp. 86.*

(Continued)

*Primary Examiner*—Daniel M Sullivan
*Assistant Examiner*—Yate' K Cutliff
(74) *Attorney, Agent, or Firm*—Millen, White, Zelano, Branigan, P.C.

(57) ABSTRACT

The present invention relates to 9-chloroprostaglandin derivatives of the general formula I which may be advantageous for the treatment of fertility problems.

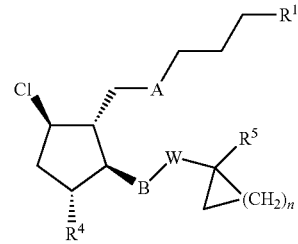

23 Claims, 3 Drawing Sheets

OTHER PUBLICATIONS

Elvin, J. et al. Growth Differentiation Factor-9 Stimulates Progesterone Synthesis Granulosa Cells via a Prostaglandin E2/EP2 receptor pathway. Aug. 2000, Proceedings of the National Academy of Science i the USA, vol. 97, No. 18, pp. 10288.*

Ota, T. et al., Prostaglandin Analogues and Mouse Intraocular Pressure: Effets of Tafluprost, latanoprost, Travoprost, and Unoprostone, Considering 24-Hour Variation, Jun. 2005, Investigative Ophthalmology & Visual Science, vol. 46, No. 6, pp. 2006.*

Akaogi, J. et al., Prostaglandin E2 receptors EP2 and EP4 are up-regulated in Peritoneal macrophages and jints of Pristan-treated Mice and Modulate TNF- and IL-6 Production, Jul. 2004, vol. 76, pp. 234 & 235.*

Dore-Duffy, P. et al., The Role of Prostaglandins in altered luekocyte Function in Multiple Sclerosis, 1985, Springer Semin Immunipathol, vol. 8, pp. 310 & 314.*

Kousake Tani et al., A Practical Synthesis and Biological Evolution of 9-Halogenated PGF Analogues, Bioorg. Med. Chem., 2002, pp. 1883-1894, 10(6).

Kousuke Tani et al., "A practical synthesis and biological evaluation of 9-halogenated PGF analogues," Bioorganic and Medicinal Chemistry, 2002, vol. 10, pp. 1883-1894.

* cited by examiner

9-CHLORO-15-DEOXYPROSTAGLANDIN DERIVATIVES, PROCESS FOR THEIR PREPARATION AND THEIR USE AS MEDICAMENTS

This application claims the benefit of U.S. provisional patent application Ser. No. 60/738,780, filed Nov. 21, 2005, the entire disclosure of which is incorporated by reference herein.

It has long been known that prostaglandins are the key molecules in the processes of female reproductive biology such as, for example, control of ovulation, of fertilisation, of nidation, of decidualisation (e.g. placenta formation) and of menstruation. Prostaglandins likewise play an important part in the pathological changes in the reproductive tract, including menorrhagia, dysmenorrhoea, endometriosis and cancer. The mechanism by which prostaglandins bring about these changes has not yet been completely elucidated. Recent results indicate that prostaglandins, their receptors and signal transduction pathways thereof are involved in processes such as angiogenesis, apoptosis and proliferation.

The effects of prostaglandins are mediated by their G protein-coupled receptors which are located on the cell surface. Prostaglandin $E_2$ ($PGE_2$) is of particular interest, having a wide variety of cellular effects through binding to functionally different receptor subtypes, namely the $EP_1$, $EP_2$, $EP_3$ and $EP_4$ receptors. Thus, it has been possible to show that reproductive functions are impaired in $EP_2$-knockout mice ($EP_2^{-/-}$), and that these animals have a smaller "litter size" (Matsumoto et al., 2001, Biology of Reproduction 64, 1557-1565). It was likewise possible to show that these $EP_2$-knockout mice (Hizaki et al. Proc Natl Acad Sci U.S.A. 1999 Aug. 31; 96(18):10501-10506) show distinctly reduced cumulus expansion and severe subfertility, demonstrating the significance of the prostaglandin $EP_2$ receptor for this process. The $EP_2$ receptor accordingly represents an important target for the development of medicaments for controlling female fertility. The 4 subclasses of the $EP_2$ receptor open up the possibility of targeted development of selectively active $PGE_2$ compounds. However, to date, scarcely any selective $EP_2$ receptor ligands are known, and most of the known compounds also bind to the other $EP_2$ receptor subtypes such as, for example, to the $EP_4$ receptor.

European patent EP 1306087 describes $EP_2$ receptor agonists which are used in the treatment of erectile dysfunction. The same structural class is described in European patent EP 860430, and their use for producing a medicament for the treatment of immunological disorders, asthma and abortion is claimed. The application WO 04/32965 describes $EP_2$ receptor agonists which are used for the treatment and prevention of disorders caused by an organ dysfunction caused by ischemia. WO 04/009117 describes $EP_2$ and $EP_4$ receptor agonists for the treatment of disorders caused by uterine contraction, for example painful menstruation.

The applications WO 03/74483 and WO 03/09872 describe agonists which bind equally to the $EP_2$ and the $EP_4$ receptor (Ono Pharmaceuticals).

Agonists of the $EP_2$ and of the $EP_4$ receptor are frequently described in connection with the treatment of osteoporosis (WO 99/19300, US 2003/0166631, WO 03/77910, WO 03/45371, WO 03/74483 and WO 03/09872) and for glaucoma treatment (WO 04/37813, WO 04/37786, WO 04/19938, WO 03/103772, WO 03/103664, U.S. Pat. No. 6,747,037, U.S. Pat. No. 6,410,591, WO 03/40123, WO 03/47513, WO 03/47417).

The patent application WO 04/12656 claims $EP_2$ receptor agonists in connection with inflammation.

The patent application WO 03/77919 claims $EP_4$ receptor agonists for the treatment of fertility. Selective $EP_2$ receptor agonists which control the processes which eventually contribute for nidation and decidualisation and thus to promotion of fertility have not to date been described.

The need to provide stable, selective and effective compounds which bind to the $EP_2$ receptor for the development of novel medicaments arises therefrom.

The abovementioned European patents of Ono Pharmaceuticals (EP 0030377 and EP 1306087) disclose prostaglandin derivatives (the Ono compounds) having a chlorine atom in position 9. The compounds claimed in these patents further comprise inter alia a hydroxy group in the lower side chain, e.g. in position 15 or 16.

SUMMARY OF THE INVENTION

The present invention relates to novel 9-chloroprostaglandin derivatives, processes for their preparation and their use as medicaments for the treatment and prophylaxis of certain disorders. Compared with prostaglandin $E_2$ and prior art derivatives, the novel $EP_2$ agonists of the present invention are distinguished by greater selectivity and stability.

DESCRIPTION OF EMBODIMENTS OF THE INVENTION

Figure 1:
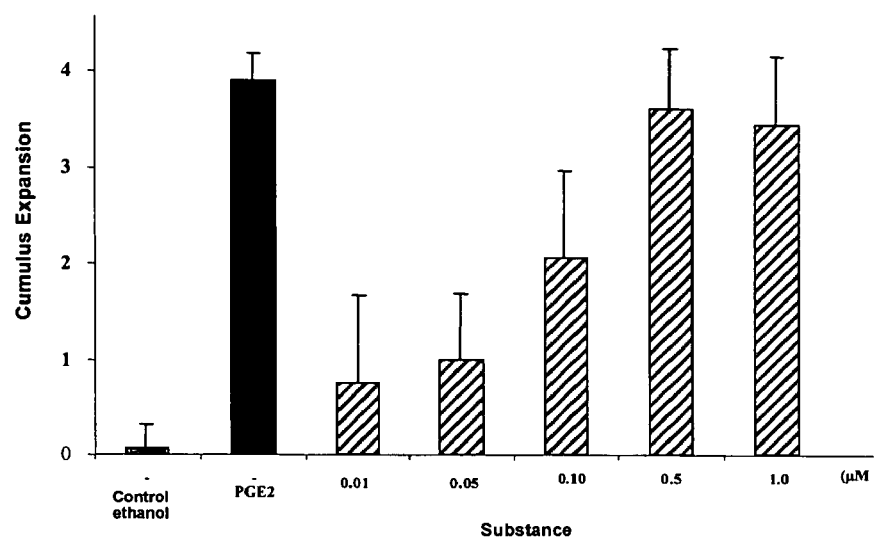
FIG. 1 shows the cumulus expansion induced by the test substance in concentrations of 0.5 µM and 1 µM. This expansion is equivalent to the cumulus expansion induced by the natural $EP_2$ receptor agonist $PGE_2$ in a concentration of 1 µM (n=16 cumulus-oocyte complexes per group).

It has surprisingly now been found that 9-chloroprostaglandin derivatives of the general Formula I:

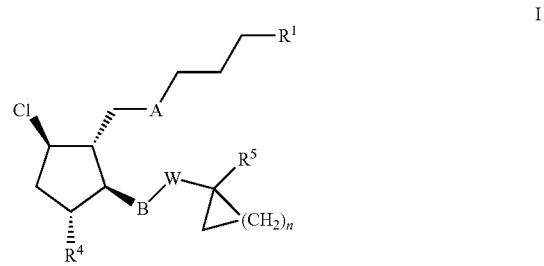

where
$R^1$ is a $CH_2OH$, $-COOR^2$, $-CONHR^2$ or $-CONHR^3$ group;
$R^2$ is a hydrogen; or
a $C_1$-$C_{10}$-alkyl radical which is linear or branched, optionally mono- to polyunsaturated, and optionally mono- to polysubstituted by halogen, $C_1$-$C_4$-alkoxy, substituted $C_3$-$C_{10}$-aryl, optionally substituted $C_3$-$C_{10}$-aroyl, optionally substituted di-$C_1$-$C_5$-alkylamino or optionally substituted tri-$C_1$-$C_5$-alkylamino; or a $C_3$-$C_{10}$-cycloalkyl which is optionally substituted by $C_1$-$C_4$-alkyl; or a $C_3$-$C_{10}$-aryl which is optionally substituted by phenyl, 1-naphthyl, 2-naphthyl which in turn may be substituted in position 3 and in position 4 by fluorine, chlorine, alkoxy or trifluoromethyl or in position 4 by hydroxy, halogen, phenyl, one or more $C_1$-$C_4$-alkyl groups, chloromethyl, fluoromethyl, trifluoromethyl, carboxy, hydroxy or $C_1$-$C_4$-alkoxy; or a $C_3$-$C_7$-heterocycloalkyl;

$R^3$ is a $C_1$-$C_{15}$-carboxylic acid or a $C_1$-$C_{15}$-sulphonic acid;

A is a cis-CH=CH— or —$CH_2$—$CH_2$— group;

B is a trans-CH=CH— or —$CH_2$—$CH_2$— group;

W is a $C_2$-$C_6$-alkylene;

$R^4$ is a hydroxy group, —O—$R^6$ or —O—$R^7$, where $R^6$ is a tetrahydropyranyl, tetrahydrofuranyl, trimethylsilyl, tert-butyidimethylsilyl, tert-butyldiphenylsilyl or tribenzylsilyl radical and $R^7$ is a $C_1$-$C_{15}$-carboxylic acid;

$R^5$ is a hydrogen, a $C_1$-$C_{10}$-alkyl or a $C_1$-$C_{10}$-alkenyl group; and n is the number 1-4;

and the salts thereof and the cyclodextrin clathrates thereof with physiologically tolerated bases, overcome the known disadvantages and, through omission of the hydroxy group in the lower side chain, exhibit a better selectivity for the $EP_2$ receptor and achieve better activity and longer duration of action, as compared to prostaglandin $E_2$ and prior art agonists such as the Ono compounds.

Alkyl groups are linear or branched alkyl groups, saturated and unsaturated alkyl radicals having 1-10 C atoms. Examples which may be mentioned are methyl, ethyl, propyl, butyl, isobutyl, tert-butyl, pentyl, neopentyl, hexyl, heptyl, octyl, decyl, butenyl, isobutenyl, propenyl, pentenyl, benzyl, m- and p-chlorobenzyl groups.

The alkyl groups may optionally be mono- to polysubstituted by halogen atoms, e.g. fluorine, chlorine or bromine; by alkoxy groups such as, for example, methoxy, ethoxy; substituted aryl or aroyl groups, e.g. phenyl; or by dialkylamino, e.g. dimethylamino, diethylamino, dimethylaminopropyl and trialkylammonium; where monosubstitution is to be preferred.

Suitable aryl groups are both substituted and unsubstituted aryl groups such as, for example, phenyl, 1-naphthyl and 2-naphthyl, each of which may be substituted by 1-3 halogen atoms, a phenyl group, 1-3 alkyl groups each having 1-4 C atoms, a chloromethyl, fluoromethyl, trifluoromethyl, carboxy, hydroxy or alkoxy group having 1-4 C atoms.

The cycloalkyl group may comprise 3-10 carbon atoms in the ring. The rings may be substituted by alkyl groups having 1-4 carbon atoms. Examples which may be mentioned are cyclopentyl, cyclohexyl, methylcyclohexyl and adamantyl.

Suitable heterocyclic groups are 5- and 6-membered heterocycles which comprise at least 1 heteroatom, preferably nitrogen, oxygen or sulphur. Examples which may be mentioned are 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, 2-tetrazolyl.

Physiologically tolerated acid residues are suitable as the acid residue. Preferred acids are organic carboxylic acids and sulphonic acids having 1-15 carbon atoms which belong to the aliphatic, cycloaliphatic, aromatic, and heterocyclic series. Examples which may be mentioned of substituents are $C_1$-$C_{15}$-alkyl, hydroxy, $C_1$-$C_{15}$-alkoxy, oxo and amino groups or halogen atoms. Examples of carboxylic acids which may be mentioned are the following: formic acid, acetic acid, propionic acid, butyric acid, isobutyric acid, valeric acid, isovaleric acid, caproic acid, oenanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid, benzoic acids substituted by halogen, trifluoromethyl, hydroxy, alkoxy or carboxy groups, nicotinic acid, isonicotinic acid, furan-2-carboxylic acid, cyclopentylpropionic acid. Examples of suitable sulphonic acids are methanesulphonic acid, ethanesulphonic acid, isopropanesulphonic acid, β-chloroethanesulphonic acid, butanesulphonic acid, cyclopentanesulphonic acid, cyclohexanesulphonic acid, benzenesulphonic acid, p-toluenesulphonic acid, p-chlorobenzenesulphonic acid, N,N-dimethylaminosulphonic acid, N,N-diethylaminosulphonic acid, N,N-bis(β-chloroethyl)aminosulphonic acid, N,N-diisobutylaminosulphonic acid, N,N-dibutylaminosulphonic acid, pyrrolidino-, piperidino-, piperazino-, N-methylpiperazino- and morpholinosulphonic acid.

The hydroxy group may be functionally modified, for example by etherification or esterification.

Suitable ether residues are the residues known to the skilled person. Preference is given to ether residues which can easily be eliminated, such as, for example, the tetrahydropyranyl, tetrahydrofuranyl, trimethylsilyl, tert-butyidimethylsilyl, tert-butyldiphenylsilyl or tribenzylsilyl radicals.

Suitable acyl radicals are the carboxylic acids mentioned under $R^7$. Examples of those which may be mentioned by name are acetyl, propionyl, butyryl and benzoyl.

Suitable for the salt formation are inorganic and organic bases as known to the skilled person for the formation of physiologically tolerated salts. Examples which may be mentioned are alkali metal hydroxides such as sodium and potassium hydroxides, alkaline earth metal hydroxides, such as calcium hydroxide, ammonia, amines such as ethanolamine, diethanolamine, triethanolamine, N-methylglucamine, morpholine, tris(hydroxymethyl)methylamine, and the like.

A "pharmaceutical composition" refers to a formulation of a compound of the invention and a medium generally accepted in the art for the delivery of the biologically active compound to mammals, for example, humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a disease or condition of interest in the mammal, preferably a human. The amount of a compound of the invention which constitutes a "therapeutically effective amount" will vary depending on the compound, the disease or condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) stabilizing the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

One embodiment of the invention is to compounds of the general formula I where:

$R^1$ is a $CH_2OH$, $-COOR^2$, $-CONHR^2$ or $-CONHR^3$ group;

$R^2$ is a hydrogen; or a $C_1$-$C_{10}$-alkyl radical which is linear or branched, optionally mono- to polyunsaturated, and is optionally mono-substituted by fluorine, chlorine, bromine, $C_1$-$C_4$-alkoxy, substituted $C_3$-$C_{10}$-aryl, optionally substituted $C_3$-$C_{10}$-aroyl, optionally substituted di-$C_1$-$C_5$-alkylamino or optionally substituted tri-$C_1$-$C_5$-alkylamino; or a $C_5$-$C_6$-cycloalkyl which is optionally substituted by $C_1$-$C_4$-alkyl; or a $C_3$-$C_{10}$-aryl radical which is optionally substituted by phenyl which may be substituted in position 3 or 4 by fluorine, chlorine, alkoxy or trifluoromethyl or in position 4 by hydroxyl; or a $C_5$-$C_6$-heterocycloalkyl which may be interrupted one or more times by nitrogen, oxygen or sulphur;

$R^3$ is a $C_1$-$C_{10}$-carboxylic acid or a $C_1$-$C_{10}$-sulphonic acid;

A is a cis-$CH=CH-$ or $-CH_2-CH_2-$ group;

B is a trans-$CH=CH-$ or $-CH_2-CH_2-$ group;

W is a $C_2$-$C_6$-alkylene;

$R^4$ is a hydroxy group;

$R^5$ is a hydrogen, a $C_1$-$C_6$-alkyl or $C_1$-$C_{10}$-alkenyl group; and n is the number 1-4, preferably 2-3.

Another embodiment of the invention is to compounds of the general formula I where:

$R^1$ is a $-CH_2OH$, $-COOR^2$ $-CONHR^2$ or $-CONHR^3$ group;

$R^2$ is a hydrogen or a $C_1$-$C_4$-alkyl which is optionally substituted by phenyl; or a $C_5$-$C_6$-cycloalkyl; or a $C_3$-$C_6$-aryl which is optionally substituted by phenyl;

$R^3$ is a $C_1$-$C_6$-carboxylic acid or a $C_1$-$C_6$-sulphonic acid;

A is a cis-$CH=CH-$ or $-CH_2-CH_2-$ group;

B is a trans-$CH=CH-$ or $-CH_2-CH_2-$ group;

W is a $C_2$-alkylene;

$R^4$ is a hydroxy group;

$R^5$ is a hydrogen, a saturated $C_1$-$C_4$-alkyl or a $C_1$-$C_5$-alkenyl; and n is the number 1-4, preferably 2-3, more preferably 2.

The invention additionally relates to a process for preparing the prostane derivatives according to the invention of the general formula I, characterized in that an aldehyde of the general formula II,

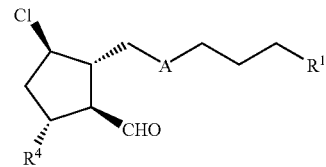

in which $R^1$ is $-COOR^2$ or $-CONHR^3$; and A and $R^4$ have the meanings indicated above, where the free OH group in $R^4$ is protected, is reacted with the carbanion of the sulphone of the general formula III

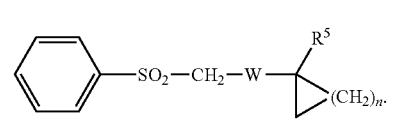

Acetylation of the resulting hydroxysulphone is followed by reductive elimination to give the olefin and, where appropriate, a subsequent deprotection of the hydroxy groups which are protected in any sequence and, where appropriate, esterification, etherification and/or hydrogenation of double bonds and/or esterification of an esterified carboxy group ($R^1=COOR^2$) and/or of a free carboxy group ($COOR^2$ with $R^2=H$) and/or conversion of a free carboxy group ($COOR^2$ with $R^2=H$) into an amide ($R^1=CONR^2$) and/or reduction of a free or esterified carboxy group ($R^1=CONHR^3$).

Reaction of the aldehyde of the general formula II with the carbanion generated from the sulphone III takes place in a manner known per se using an inert solvent such as, for example, tetrahydrofuran or diethyl ether at temperatures between –100° C. and 24° C., preferably –100° C. to –70° C. The carbanion of the sulphone III is generated in a conventional way with a base such as, for example, butyllithium, methyllithium, potassium tert-butoxide, sodium hydride, lithium diisopropylamide, preferably butyllithium. The carbanion formation is carried out at temperatures from –78° C. to 25° C., preferably at –78° C.

Acetylation of the generated hydroxy group takes place in a known manner with acetic anhydride, where appropriate in the presence of a base, for example pyridine, at temperatures between –78° C. and 25° C.

Reductive elimination of the intermediate acetoxy sulphone to give the trans-olefin of the general formula I takes place with magnesium powder in methanol with the addition of a catalytic amount of chlorotrimethylsilane. The reaction is carried out at temperatures between 0° C. and 60° C., preferably between 15° C. and 25° C. Alternatively, the reductive elimination can also be carried out with sodium amalgam.

Reduction to give the compounds of the general formula I with $R^1$ in the meaning of a $-CH_2OH$ group is carried out with a reducing agent suitable for reducing esters or carboxylic acids, such as, for example, lithium aluminium hydride, diisobutylaluminium hydride etc. Suitable solvents are diethyl ether, tetrahydrofuran, dimethoxyethane, toluene etc. The reduction is carried out at temperatures from –30° C. to the boiling point of the solvent used, preferably 0° C. to 30° C.

Functionally modified hydroxy groups are liberated by known methods. For example, elimination of hydroxy protective groups such as, for example, the tetrahydropyranyl radical is carried out in an aqueous solution of an organic acid, such as, for example, oxalic acid, acetic acid, propionic acid, inter alia, or in an aqueous solution of an inorganic acid such as, for example, hydrochloric acid. It is expedient to add a water-miscible inert organic solvent to improve the solubility. Examples of suitable organic solvents are alcohols such as methanol and ethanol, and ethers such as dimethoxyethane, dioxane and tetrahydrofuran. Tetrahydrofuran is preferably used. The elimination is preferably carried out at temperatures between 20° C. and 80° C.

The acyl groups are hydrolysed for example with alkali metal or alkaline earth metal carbonates or hydroxides in an alcohol or in the aqueous solution of an alcohol. Suitable alcohols are aliphatic alcohols such as, for example, methanol, ethanol, butanol etc., preferably methanol. Alkali metal carbonates and hydroxides which may be mentioned are potassium and sodium salts. The potassium salts are preferred. Examples of suitable alkaline earth carbonates and hydroxides are calcium carbonate, calcium hydroxide and barium carbonate. The reaction takes place at from −10° C. to +70° C., preferably at +25° C.

The ester group —$COOR^2$ for $R^1$, for example in which $R^2$ is an alkyl group having 1-10 C atoms, is introduced by the methods known to the skilled person. The 1-carboxy compounds are reacted for example with diazohydrocarbons in a manner known per se. Esterification with diazohydrocarbons takes place for example by mixing a solution of the diazohydrocarbon in an inert solvent, preferably in diethyl ether, with the 1-carboxy compound in the same or in a different inert solvent, such as, for example, methylene chloride. After the reaction is complete in 1 to 30 minutes, the solvent is removed and the ester is purified in a conventional way. Diazoalkanes are either known or can be prepared by known methods (Org. Reactions Vol. 8, pages 389-394 (1954)).

The ester group $COOR^2$ for $R^1$, in which $R^2$ is a substituted or unsubstituted aryl group, is introduced by the methods known to the skilled person. For example, the 1-carboxy compounds are reacted with the appropriate aryl hydroxy compounds with dicyclohexylcarbodiimide in the presence of a suitable base, for example pyridine, DMAP or triethylamine, in an inert solvent. Suitable solvents are methylene chloride, ethylene chloride, chloroform, ethyl acetate, tetrahydrofuran, preferably chloroform. The reaction is carried out at temperatures between −30° C. and +50° C., preferably at 10° C.

If it is intended to reduce C=C double bonds present in the initial product, the hydrogenation takes place by methods known per se.

Hydrogenation of the 5,6 double bond is carried out in a manner known per se at low temperatures, preferably at about −20° C., in a hydrogen atmosphere in the presence of a noble metal catalyst. An example of a suitable catalyst is 10% palladium on carbon.

If both the 5,6 double bond and the 13,14 double bond are hydrogenated, a higher temperature is used, preferably about 20° C.

The prostaglandin derivatives of the general formula I where $R^2$ is a hydrogen atom can be converted into a salt by neutralization using suitable amounts of the appropriate inorganic bases. For example, dissolving the appropriate prostaglandin acids in water containing the stoichiometric amount of the base results, after the water has been evaporated off or a water-miscible solvent, e.g. alcohol or acetone, has been added, in the solid organic salt.

An amine salt is prepared in a conventional way by dissolving the prostaglandin acid for example in a suitable solvent, for example ethanol, acetone, diethyl ether, acetonitrile or benzene, and adding at least the stoichiometric amount of the amine to this solution. This usually results in the salt in solid form, or it is isolated in the usual way after evaporation of the solvent.

The amide group —$CONHR^3$ for $R^1$ is introduced by methods known to the skilled person. The carboxylic acids of the general formula I ($R^2$=H) are initially converted into the mixed anhydride with isobutyl chloroformate in the presence of a tertiary amine such as, for example, triethylamine. Reaction of the mixed anhydride with the alkali metal salt of the appropriate amine or with ammonia ($R^3$=H) takes place in an inert solvent or solvent mixture, such as, for example, tetrahydrofuran, dimethoxyethane, dimethylformamide, hexamethylphosphoric triamide, at temperatures between −30° C. and +60° C., preferably at 0° C. to 30° C.

A further possibility for introducing the amide group —$CONHR^3$ for $R^1$ consists in reacting a 1-carboxylic acid of the general formula I ($R^2$=H), in which there is optionally intermediate protection of free hydroxy groups, with compounds of the general formula IV $$O=C=N-R^3 \qquad\qquad IV$$

in which $R^3$ has the meaning indicated above.

Reaction of the compound of the general formula I ($R^2$=H) with an isocyanate of the general formula IV takes place where appropriate with addition of a tertiary amine such as, for example, triethylamine or pyridine. The reaction can be carried out without solvent or in an inert solvent, preferably acetonitrile, tetrahydrofuran, acetone, dimethylacetamide, methylene chloride, diethyl ether, toluene, at temperatures between −80° C. to 100° C., preferably at 0° C. to 30° C.

If the starting material comprises OH groups in the prostane residue, these OH groups are also reacted. If the final products eventually desired comprise free hydroxy groups in the prostane residue, it is expedient to start from starting materials with intermediate protection thereof by ether or acyl radicals which can preferably be easily eliminated.

The aldehydes of the general formula II which are used as starting material are known or can be prepared for example by selective epoxidation in a manner known per se of the 13,14 double bond of a 9-haloprostaglandin of the general formula V, preferably with $R^1$ meaning a —$COOCH_3$ group, with tert-butyl hydroperoxide and titanium(IV) isopropoxide in methylene chloride at −20° C.

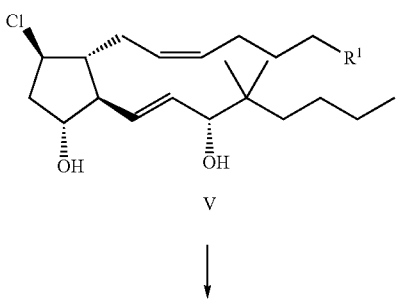

V

↓

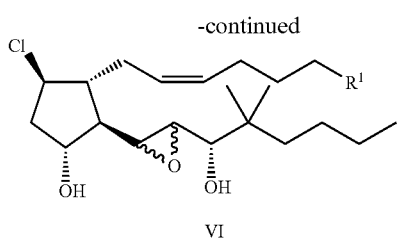

VI

Subsequent epoxide cleavage with periodic acid in diethyl ether and, where appropriate, protection of the 11-hydroxy group, for example with dihydropyran, affords the aldehyde of the general formula II.

The sulphone of the general formula III used as starting material can be prepared from cycloalkylcarboxylic acids of the general formula VII in which n has the meaning indicated above by alkylation with an alkyl halide of the general formula VIII in which $R^5$ has the meaning indicated above, and halogen can be iodine, chlorine or bromine.

toluene. The thioether XIII obtained in this way is finally oxidized in an aqueous methanolic solution to the sulphone of the general formula III.

Compared with prostaglandin $E_2$, the novel $EP_2$ agonists are distinguished by greater selectivity and stability. The novel prostaglandin analogues of the $EP_2$ type are suitable, for example, for the treatment and prophylaxis of disorders which include fertility disorders, infectious diseases, cancer, viral infections, cardiovascular disorders, elevated intraocular pressure, glaucoma, disorders of the skeletal system, angiogenic disorders, abnormalities of uterine contraction, pain and nephrological disorders.

By fertility disorders are meant disorders leading to no ovulation taking place, to the ovulated oocyte/cumulus cell complex not being fertilisable, to nidation of a fertilised oocyte not taking place and no decidualisation taking place; by infectious diseases are meant diseases caused by unicellular parasites; by cancer are meant solid tumours and leukaemia; by viral infections are meant cytomegalovirus infections, hepatitis, hepatitis B and C, and HIV disorders; by cardiovascular disorders are meant ischemic reperfusion dis-

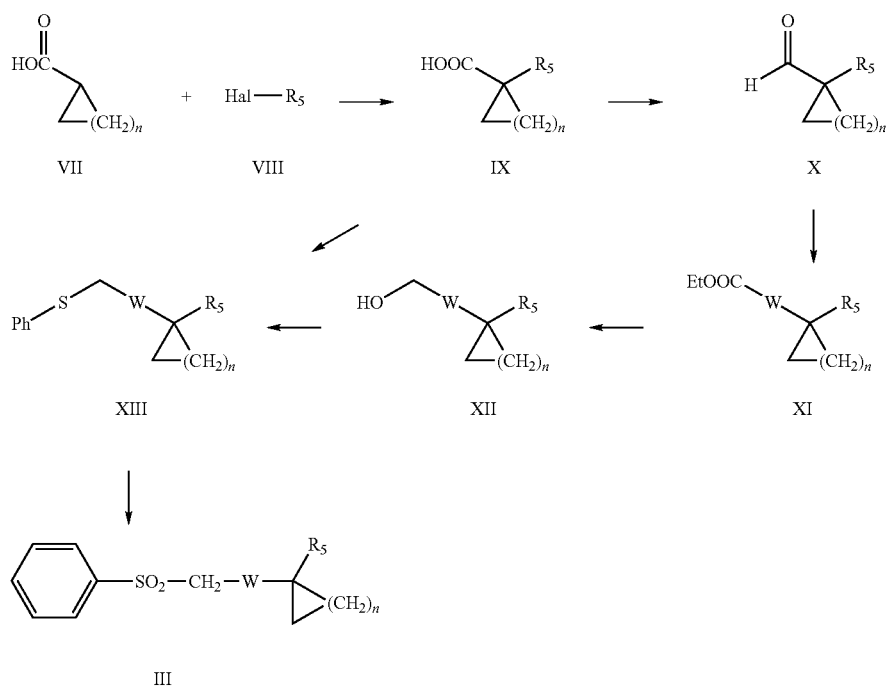

Esterification of IX with methyl iodide and potassium carbonate in acetone is followed by reduction of the resulting methyl ester to the alcohol with lithium aluminium hydride in diethyl ether. Oxidation of the alcohol with $SO_2$-pyridine complex in the presence of triethylamine in a mixture of dimethyl sulphoxide and methylene chloride affords the aldehyde of the general formula X. Subsequent Wittig-Horner reaction and, where appropriate, hydrogenation of the double bond to give XI leads, after reduction with diisobutylaluminium hydride, to the alcohol of the general formula XII. Hydrogenation of the double bond can, however, also be carried out after reduction of the ester XI to the alcohol XII, with W meaning a double bond.

Subsequent replacement of the hydroxy group takes place after intermediate tosylation by reaction with thiophenol in order, stenoses, arterioscleroses and restenoses; by angiogenic disorders are meant, for example, endometriosis; by elevated intraocular pressure is meant glaucoma; by abnormalities of uterine contraction are meant, for example, painful menstruation; by disorders of the skeletal system are meant osteoporosis; and by nephrological disorders are meant glomerulonephritis.

For use of the compounds according to the invention as medicaments, they are converted into the form of a pharmaceutical composition that, besides the active ingredient, comprises pharmaceutical, organic or inorganic inert carrier materials suitable for enteral or parenteral administration, such as, for example, water, gelatin, gum arabic, lactate, starch, magnesium stearate, talc, vegetable oils, polyalkylene glycols, etc. The pharmaceutical compositions may be in solid form, for example as tablets, coated tablets, suppositories or capsules, or in liquid form, for example as solutions, suspensions or emulsions. They additionally comprise, where appropriate, excipients such as preservatives, stabilizers, wetting agents or emulsifiers, salts to alter the osmotic pressure or buffers.

The present invention likewise relates to these pharmaceutical products:

Aerosol solutions are expediently produced by inhalation.

Particularly suitable for oral use are tablets, coated tablets or capsules with talc and/or carbohydrate carriers or binders, such as, for example, lactose, maize starch or potato starch. Use is also possible in liquid form, such as, for example, as fluid to which a sweetener is added where appropriate.

Sterile, injectable, aqueous or oily solutions are used for parenteral administration. Solutions for injection or suspensions are particularly suitable, especially aqueous solutions of the active compounds in polyethoxylated castor oil are suitable.

Suppositories for example are suitable and customary for vaginal administration.

Carrier systems which can also be used are surface-active excipients such as salts of bile acids or animal or vegetable phospholipids, but also mixtures thereof, and liposomes or constituents thereof.

The present invention likewise relates to the enteral, parenteral, vaginal and oral administrations.

The compounds of the invention are administered to a patient in need thereof in a therapeutically effective amount. By a "therapeutically effective amount" is meant an amount or dosage necessary to treat or prevent a particular disorder, which amount or dosage can be determined by methods known in the art without undue experimentation. The dosage of the active ingredient may vary depending on the route of administration, the age and weight of the patient, the nature and severity of the disorder to be treated and similar factors. The daily dose is generally from about 0.5 to about 1000 mg, preferably about 50-200 mg, it being possible for the dose to be given as a single dose to be administered once or divided into 2 or more daily doses.

The present invention likewise relates to medicaments for the treatment of the disorders listed herein, which comprise at least one compound according to the general formula I, and medicaments with suitable formulating substances and carriers.

The present invention likewise relates to the use of the compounds of the general formula (I) for producing a medicament for the treatment and prophylaxis of disorders which include fertility disorders, infectious diseases, cancer, viral infections, cardiovascular disorders, elevated intraocular pressure, glaucoma, disorders of the skeletal system, angiogenic disorders, abnormalities of uterine contraction, pain and nephrological disorders.

By fertility disorders are meant disorders leading to no ovulation taking place, to the ovulated oocyte/cumulus cell complex not being fertilisable, to nidation of a fertilised oocyte not taking place and no decidualisation taking place, by infectious diseases are meant diseases caused by unicellular parasites, by cancer are meant solid tumours and leukaemia, by viral infections are meant cytomegalovirus infections, hepatitis, hepatitis B and C and HIV disorders, by cardiovascular disorders are meant ischemic reperfusion disorder, stenoses, arterioscleroses and restenoses, by angiogenic disorders are meant for example endometriosis, by elevated intraocular pressure is meant glaucoma, by abnormalities of uterine contraction are meant for example painful menstruation, by disorders of the skeletal system are meant osteoporosis and by nephrological disorders are meant glomerulonephritis.

The compounds according to the invention of the general formula I bind to the $EP_2$ receptor and have agonistic action. The binding of $PGE_2$ to the $EP_2$ subtype of the human $PGE_2$ receptor induces the activation of membrane-associated adenylate cyclases and leads to the formation of cAMP.

FIG. 1 shows a very high activity (EC50<9.5×10e−5M), in the cellular agonism test without any inhibition in the antagonism test ($IC_{50}$>2×10e−5M).

The present invention likewise relates to the use of the substances according to the invention as $EP_2$ receptor agonists.

The compounds according to the invention of the general formula I have a profertile effect. The oocyte is surrounded in the preovulatory antral follicle by cumulus cells which form a dense ring of cells around the oocyte. After the lutenising hormone peak (LH peak), a series of processes is activated and leads to a large morphological change in this ring of cells composed of cumulus cells. In this case, the cumulus cells form an extracellular matrix which leads to so-called cumulus expansion (Vanderhyden et al. Dev Biol. 1990 August; 140 (2):307-317). This cumulus expansion is an important component of the ovulatory process and of the subsequent possibility of fertilisation.

Prostaglandins, and here prostaglandin $E_2$, whose synthesis is induced by the LH peak, are of crucial importance in cumulus expansion. Prostanoid $EP_2$ knockout mice (Hizaki et al. Proc Natl Acad Sci USA. 1999 Aug. 31; 96(18):10501-6) show a markedly reduced cumulus expansion and severe subfertility, demonstrating the importance of the prostanoid $EP_2$ receptor for this process.

The $EP_2$ agonist leads to a concentration-dependent large expansion in the cumulus complex. The cumulus expansion induced by the test substance is equivalent in concentrations of 0.5 µM and 1 µM to the cumulus expansion induced by the natural $EP_2$ receptor agonist $PGE_2$ in a concentration of 1 µM (n=16 cumulus-oocyte complexes per group; see FIG. 1).

Figure 2:
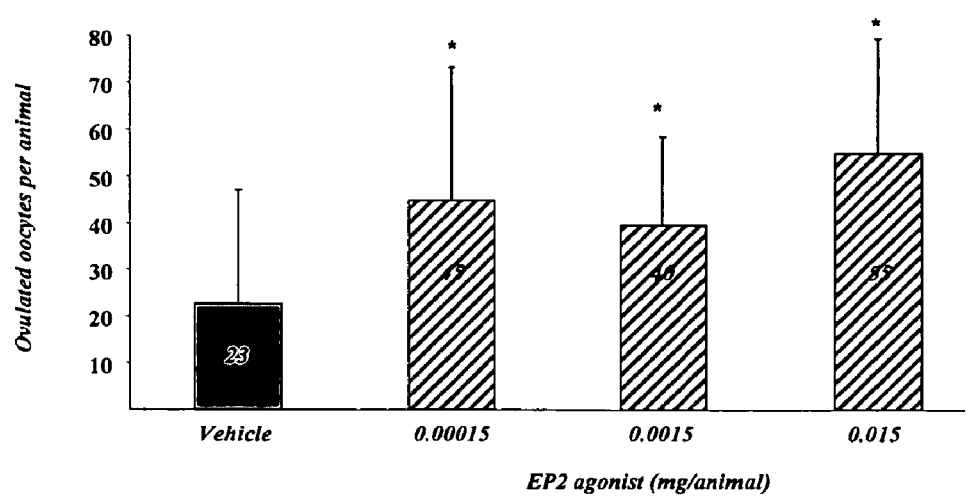
FIG. 2 shows the ovulation induced by the test substance in vivo. The test substance is administered in concentrations of 0.00015, 0.0015 and 0.015 mg/animal 10, 5 and 0 hours before HCG.

The $EP_2$ agonist leads to a concentration-dependent significant increase in ovulated oocytes. This significant increase in ovulated oocytes occurs on administration of only 0.00015 mg/animal in each case and shows that it is possible to increase the number of ovulated oocytes even with a standard dose of HCG used for ovulation (n=11-12 animals per group; **p<0.005 and *p<0.05), FIG. 2).

The present invention likewise relates to the use of the compounds according to the invention for the treatment of fertility disorders such as impaired or absent ovulation, impaired fertilisation of the oocyte/cumulus cell complex, impaired implantation and impaired decidualisation.

Prostaglandins play an important part in angiogenesis (Sales, Jabbour, 2003, Reproduction 126, 559-567).

Endometriosis is a chronic disorder caused by impairments of blood vessels. About 10% of women regularly suffer from heavy bleeding during menstruation, caused by changes in the blood vessels of the endometrium. In addition, structural differences in the blood vessels have been observed, such as, for example, incomplete formation of the smooth muscle cell layer (Abberton et al. 1999, Hum. Reprod. 14, 1072-1079). Since the blood loss during menstruation is partly controlled by constriction of the blood vessels, it is obvious that the defects in the smooth muscles make a substantial contribution to the bleeding.

Prostaglandins and effects mediated by the $EP_2$ receptor likewise play a part in the hormonal regulation of endometriotic lesions (Sun et al. 2003, Endocrinology 144, 3934-3942).

Growing evidence suggests that endometriosis is associated with a significant inflammatory response that may be mediated by activated macrophages and lymphocytes and increased levels of cytokines, chemokines, and growth factors. These inflammatory processes have been hypothesised to mediate some of the clinical features associated with endometriosis. The peritoneal fluid of women with endometriosis is known to contain more inflammatory cells and their associated cytokines, chemokines, and growth factors. (Murphy A A. Clinical aspects of endometriosis. Ann NY Acad Sci. March 2002;955:1-10). The result is an environment that promotes implantation and proliferation.

Prostaglandins, and here prostaglandin $E_2$, reduces the expression of inflammatory cytokines, such as TNFα, from activated macrophages. Prostanoid $EP_2$ knockout mice (Shinomiya S et al. Regulation of TNFα and IL-10 production by prostaglandins I2 and E2: studies with prostaglandin receptor-deficient mice and prostaglandin E-receptor subtype-selective synthetic agonists, Bioch Phar 2001; 61:1153) fail to respond to $EP_2$ agonists, demonstrating the importance of the prostanoid $EP_2$ receptor for this process.

Figure 3:
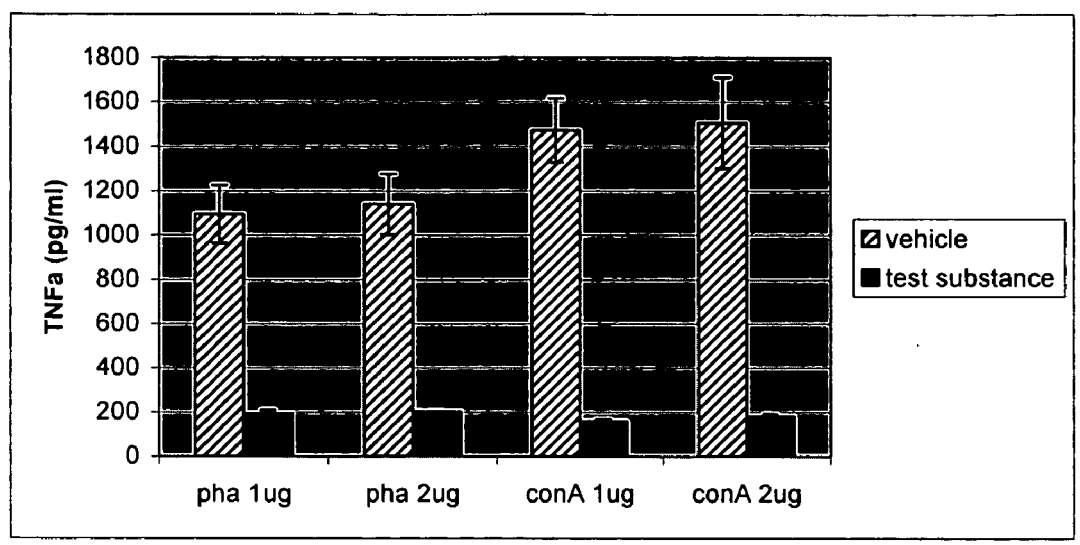
FIG. 3 shows the effect by the test substance on ex vivo mouse splenocyte activation. Cells are activated with PHA or ConA. The test substance is administered intraperitoneally in concentrations of 1 and 2 µg/animal 20 min before sacrifice.

Table 1 shows that an $EP_2$ agonist of the invention leads to an inhibition in the cytokine levels measured in the culture supernatant. The $EP_2$ agonist also causes a significant decrease in TNFα as shown in FIG. 3. The present invention relates to the use of the compounds of the general formula I for the treatment of endometriosis.

TABLE 1

Inhibition of TNFα Release from activated monocytic cells

| Test Substance + LPS | Donor 4 (TNFα pg/ml) | Donor 6 (TNFα pg/ml) |
|---|---|---|
| Vehicle | 3566.9 | 10750.1 |
| PGE2 | 0.0 | 174.8 |
| Test substance | 643.6 | 753.7 |

| Test Substance + CD40 ligand | Donor 3 (TNFα pg/ml) | Donor 4 (TNFα pg/ml) | Donor 6 (TNFα pg/ml) |
|---|---|---|---|
| Vehicle | 567.1 | 546.3 | 541.8 |
| PGE2 | 147.9 | 87.0 | 54.2 |
| Test substance | 274.3 | 226.8 | 142.4 |

| Test Substance + CpG | Donor 1 (TNFα pg/ml) | Donor 3 (TNFα pg/ml) | Donor 6 (TNFα pg/ml) |
|---|---|---|---|
| Vehicle | 2155.9 | 1340.7 | 467.8 |
| PGE2 | 104.5 | 70.0 | 106.2 |
| Test substance | 291.3 | 599.4 | 115.9 |

Table 1 shows the effect of test substance on the TNFα release from activated monocytic cells in vitro. The test substance is administered in a concentration of 1 μM. Cells are activated for 18 hours. Test substance shows dose-responsively very high inhibitory activity in the T lymphocyte Th-1 cytokine release.

Prostaglandins play an important part in uterine contraction, and excessively strong contractions are responsible for painful menstruation (Sales, Jabbour, 2003, Reproduction 126, 559-567). The present invention relates to the use of the substances of the general formula I for the treatment of painful menstruation.

EP2 receptor agonists additionally play a significant part in controlling the intraocular pressure. It has been possible to show that, in particular, $EP_2$ receptors are present in high concentrations in the vessels of the trabecular meshwork (TM) of the eye. Tears leave the eye via the TM and Schlemm's canal, and $EP_2$ receptor agonists influence the dynamics of tear fluid by stimulating outflow of tear fluid and thus leading to a reduction in the intraocular pressure. (W. Kamphuis et al. Current Eye Res. 2004, 29:17-26). The present invention relates to the use of the substances according to the invention for the treatment of elevated intraocular pressure as associated inter alia with glaucoma.

Prostaglandins also play an important part in processes counteracting osteoporosis. The present invention therefore relates to the use of the substances according to the invention for the treatment of osteoporosis.

Prostaglandins also play an important part in processes controlling blood pressure. The present invention therefore relates to the use of the substances according to the invention for the treatment of high blood pressure.

Prostaglandins also influence the production of cytokines. Multiple Sclerosis (MS) is considered as a systemic T lymphocyte-mediated autoimmune disease whose target tissue is the central nervous system. T lymphocytes cytokine release profiles may be skewed to either the T helper 1 or T helper 2 (Th-1 or Th-2) lineage. Th-1 cells secrete cytokines such as interferon gamma (INF-γ) and induce a cell-mediated immune response, whereas Th-2 cells secrete IL-4, IL-5 and IL-10 and induce a humoral or antibody-mediated response [Mossman et al. 1989, Annual Rev Immunol. 7: 145-173]. INF-γ expression is associated with MS and using a multifactorial measure of disability, the expression of IFN-γ in response to PLP peptides and MBP peptides is significantly correlated with disability [Hirsch et al. 1985, J. Clin Immunol November; 5(6):386-389; Moldovan et al. 2003, J. Neuroimmunol. August; 141(1-2):132-140]. Importantly, clinical studies show that administration of IFN-γ causes exacerbations in MS patients [Panitch et al., Lancet, April 18; (8538): 893-895].

Table 2 demonstrates the effect of test substance on the inhibition of T lymphocyte Th-1 cytokine release. The test substance is added dose dependently (0-20 nM) to cells during their activation by ConA, cells are incubated for 18 hours. Table 2 shows that the $EP_2$ agonist of the invention leads to an inhibition of INF-γ expression from activated human donor T cells in the activated T cell assay.

TABLE 2

Inhibition of T lymphocyte Th-1 cytokine release

| | % inhibition below untreated, ConA stimulated control (±standard deviation) | |
|---|---|---|
| Test substance [nM] | Donor 1 | Donor 2 |
| 0 | 0 ± 6 | 0 ± 13 |
| 0.5 | 5 ± 5 | 7 ± 22 |
| 1.12 | 8 ± 4 | 28 ± 27 |
| 2.5 | 33 ± 13 | 36 ± 14 |
| 5 | 52 ± 11 | 56 ± 7 |
| 10 | 70 ± 8 | 74 ± 3 |
| 20 | 84 ± 1 | 81 ± 6 |

Tables 3 a) and b) demonstrate the effect of test substance on the inhibition of human monocytes derived dendrite cell cytokine release. Test substance or $PGE_2$ is added at a concentration of 1 μM during stimulation of cells with LPS. Cells are incubated for 18 hours. The test compound shows high immunomodulatory activity in the human monocyte derived dendritic cell (DC) cytokine release assay and a suppression of the Th-1 promoting cytokine IL-12 (3a) while it spared, in fact increased, the Th-2 promoting cytokine IL-10 (3b). Table 3 shows a downregulation of Th-1-associated cytokines in an activated human donor monocyte-derived dendritic cell assay in the presence of an $EP_2$ agonist of the invention.

TABLE 3a

Inhibition of human monocyte derived dendritic cell cytokine release, measurement of IL-12 (pg/ml)

| Donor | % inhibition below untreated, LPS-stimulated control | |
|---|---|---|
| | Test substance [1 μM] | $PGE_2$ [1 μM] |
| 1 | 64 | 78 |
| 2 | 7 | 44 |
| 3 | 38 | 84 |
| 4 | 29 | 29 |

TABLE 3 b

Inhibition of human monocyte derived dendritic cell cytokine release, measurement of IL-10 (pg/ml)

| Donor | % inhibition below untreated, LPS-stimulated control | |
|---|---|---|
| | Test substance [1 μM] | $PGE_2$ [1 μM] |
| 1 | 144 | 103 |
| 2 | 168 | 134 |
| 3 | 153 | 107 |

Therefore, both by inhibiting INF-γ expression directly and by skewing the dendritic cell-mediated polarization of CD4+ T cells away from the Th-1 lineage that express INF-γ, the $EP_2$ agonist is predicted to reduce the expression of INF-γ in MS patients.

The present invention likewise relates to the use of the compounds according to the invention for the treatment of autoimmune diseases such as autoimmune disease is selected from the group consisting of multiple sclerosis, secondary progressive multiple sclerosis, psoriasis, rheumatoid arthritis, Crohn's disease, and alopecia areata.

Where the preparation of the starting compounds is not described, they are known or can be prepared in analogy to known compounds or to processes described herein. It is likewise possible to carry out all the reactions described herein in parallel reactors or by means of combinatorial operating techniques.

Mixtures of isomers can be fractionated by conventional methods such as, for example, crystallization, chromatography or salt formation into the enantiomers or E/Z isomers.

Salts are prepared in a conventional way by adding the equivalent amount or an excess of a base or acid, which is in solution where appropriate, to a solution of the compound of the formula I, and separating off the precipitate or working up the solution in a conventional way.

The invention thus also relates to medicaments based on the compounds of the general formula I and conventional excipients or carriers.

The following examples are intended to explain the invention in detail without a limitation being undertaken thereby.

EXAMPLES

Synthesis Example 1

Methyl (5Z,13E)-(9R,11R)-9-chloro-11-[(2H)-tetrahydropyran-2-yloxy]-17,17-tetramethylene-20-nor-5,13-prostadienoate 0.68 mL of a 1.6 M butyllithium solution in hexane is added dropwise to a solution of 290 mg of 1-phenylsulphonyl-4,4-(trimethylene)hexane in 2.4 mL of tetrahydrofuran at −78° C. under nitrogen, and the mixture is stirred at −78° C. for 1.5 hours. This solution is then added dropwise at −100° C. to a solution of 315 mg of aldehyde (of Example 1c) in 2.4 mL of tetrahydrofuran. The mixture is then stirred at −100° C. for 30 min and at −78° C. for 1 h. Then 0.16 mL of acetic anhydride is added to the reaction mixture, and the mixture is warmed to room temperature over the course of 1 h. The reaction mixture is mixed with ammonium chloride solution and extracted 3× with ethyl acetate, and the combined organic phases are washed 1× with water and 1× with saturated sodium chloride solution, dried over sodium sulphate and concentrated in vacuo. The intermediate is dissolved in 6 mL of methanol and, under nitrogen, 160 mg of magnesium powder are added. The mixture is then stirred at room temperature for 15 min. One drop of chlorotrimethylsilane is then added to the reaction mixture, and the mixture is stirred at room temperature for a further 3 h. The reaction mixture is added to 5 mL of ice-cold ammonium chloride solution and extracted 3× with ethyl acetate, and the combined organic phases are washed 1× with water and 1× with saturated sodium chloride solution, dried over sodium sulphate and concentrated in vacuo. Chromatography on silica gel with hexane/ethyl acetate (8:2) results in 140 mg of the ester.

$^1$H-NMR (CDCl$_3$): δ=0.75 (3H), 1.4-2.4 (30H), 3.44 (1H), 3.66 (3H), 3.8-4.15 (3H), 4.63 (1H), 5.15-5.65 (4H)

The starting aldehyde is prepared as follows:

1a) Methyl (5Z)-(9R,11R,13RS,14RS,15S)-9-chloro-11,15-dihydroxy-16,16-dimethyl-13,14-epoxy-5-prostenoate 4.7 mL of titanium(IV) isopropoxide are added dropwise to a solution of 6.52 g of methyl (5Z,13E)-(9R,11R,15R)-9-chloro-11,15-dihydroxy-16,16-dimethyl-5,13-prostadienoate in 33 mL of methylene chloride at −20° C. under nitrogen, and the mixture is stirred at −20° C. for 30 min. Six mL of tert-butyl hydroperoxide are then added to the reaction mixture. A solution of 10 g of iron sulphate and 20 g of citric acid in 100 mL of water is subsequently added, and the mixture is extracted 3× with methylene chloride. The combined organic phases are washed 1× with saturated sodium chloride solution, dried over sodium sulphate and concentrated in vacuo. Chromatography on silica gel with methylene chloride/ethyl acetate (0-40%) results in 3.55 g of the epoxide as a colourless oil.

$^1$H-NMR (CDCl$_3$): δ=0.75-1.05 (9H), 1.1-2.4 (18H), 2.9-3.0 (2H), 3.2 (1H), 3.65 (3H), 4.0-4.15 (2H), 4.63 (1H), 5.3-5.55 (2H)

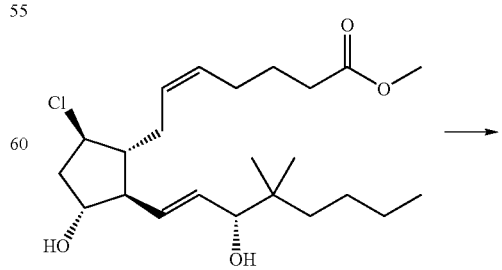

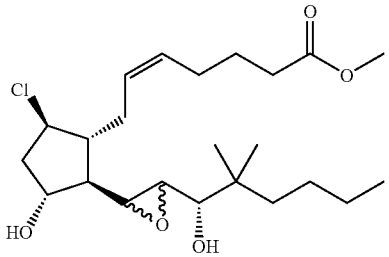

1b) Methyl (5Z)-(9R,11R)-9-chloro-11-hydroxy-14,15,16,17,18,19,20-heptanor-12-oxo-5-prostenoate 5 Grams of periodic acid are vigorously stirred in 360 mL of ether under nitrogen for 1 h. 125 mL of this solution are added to a solution of 2 g of the epoxide in 5 mL of ether, and the mixture is stirred under nitrogen at room temperature. After 1 h, a further 125 mL of periodic acid solution are added to the reaction mixture and, after 2 h, the remainder of the periodic acid solution is added. After filtration, the filtrate is washed 1× with saturated sodium bicarbonate solution, 1× with water and 1× with saturated sodium chloride solution, dried over sodium sulphate and concentrated in vacuo. Yield: 1.9 g of the aldehyde.

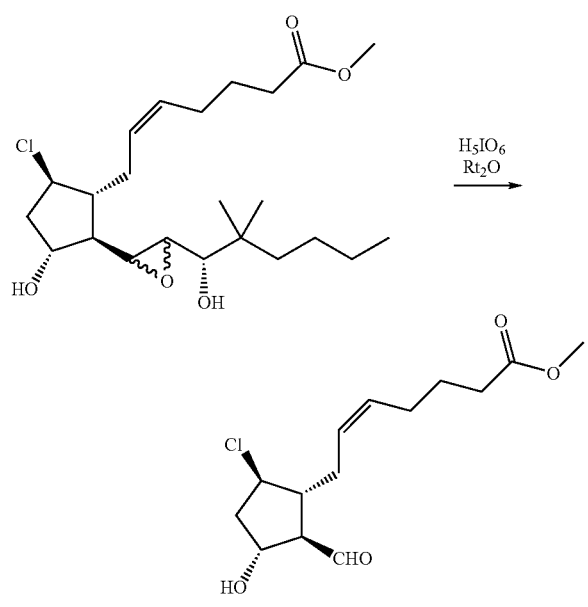

1c) Methyl (5Z)-(9R,11R)-9-chloro-11-[(2H)-tetrahydropyran-2-yloxy]-14,15,16,17,18,19,20-heptanor-12-oxo-5-prostenoate 1.9 Grams of the aldehyde are dissolved in 20 mL of methylene chloride and mixed with 1.6 mL of dihydropyran and 8.8 mg of pTsOH and stirred for 30 min. The mixture is then diluted with ether, washed 1× with saturated sodium bicarbonate solution and 1× with saturated sodium chloride solution, dried over sodium sulphate and concentrated in vacuo. Chromatography on silica gel twice [1st column: methylene chloride/ethyl acetate (2-10%), 2nd column: hexane/ethyl acetate (0-20%)] results in 720 mg of the tetrahydropyranyl ether.

$^1$H-NMR (CDCl$_3$): δ=1.35-2.7 (17H), 3.65 (3H), 3.4-4.1 (3H), 4.58 (2H), 5.3-5.55 (2H), 9.75 (1H)

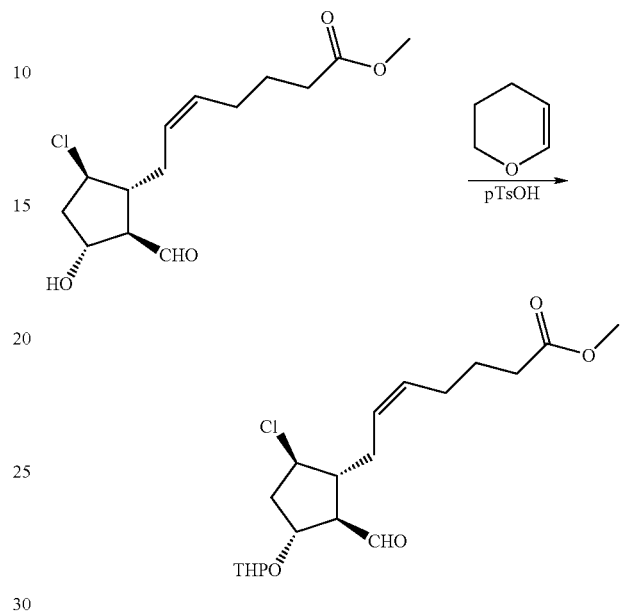

Preparation of the Sulphone 1d) 2,2-(Trimethylene)butanic acid

A solution of 61.6 mL of diisopropylamine in 180 mL of tetrahydrofuran is added dropwise to 275 mL of butyllithium (1M in hexane) at −10° C. under nitrogen, and the mixture is stirred at −10° C. for 30 min. At −20° C., 19.1 mL of cyclobutanecarboxylic acid are added dropwise to the reaction mixture, and the reaction mixture is stirred for 4 hours, during which it warms to room temperature. The suspension is poured into 300 mL of ice-water, adjusted to pH 1 with 2N hydrochloric acid and extracted 4× with 300 mL of ether each time, and the combined organic phases are washed 1× with saturated sodium chloride solution, dried over sodium sulphate and concentrated in vacuo. Yield: 30.1 g of the carboxylic acid.

$^1$H-NMR (CDCl$_3$): δ=0.88 (3H), 1.75-1.95 (6H), 2.4 (2H)

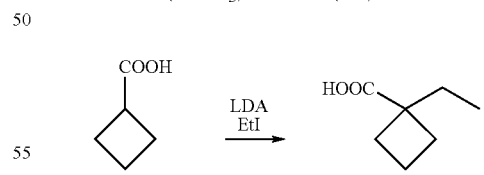

1e) 2,2-Trimethylenebutan-1-al 62.2 Grams of potassium carbonate and 28 mL of methyl iodide are added to a solution of 25.6 g of 1d) in 300 mL of acetone at room temperature under nitrogen, and the mixture is stirred for 12 hours. The precipitate is then filtered off with suction, and the filtrate is concentrated in vacuo at room temperature. The crude product is dissolved in 500 mL of ether and washed 1× with water and 1× with saturated sodium chloride solution, and the organic phase is dried over sodium sulphate and concentrated in vacuo. The residue is distilled in vacuo at 85 mbar and 110° C. (boiling point 85-90° C.). Yield: 24.5 g of the ester.

20 Grams of the ester are dissolved in 40 mL of ether, this solution is added dropwise to a suspension of 4.8 g of lithiumaluminium hydride in 390 mL of ether at 0° C. under nitrogen, and the mixture is stirred at 0° C. for one hour and then at room temperature for 1 hour. The excess lithiumaluminium hydride is decomposed very cautiously, at 0° C., with 11 mL of water, 11 mL of 15% strength sodium hydroxide solution and again with 30 mL of water. Stirring for 20 minutes is followed by filtration and then extensive washing with ether, and the filtrate is dried over sodium sulphate and concentrated in vacuo. Yield: 16.3 g of the alcohol.

48 mL of triethylamine and 22.27 g of $SO_3$-pyridine complex are added to a solution of 8 g of alcohol in 450 ml of methylene chloride and 100 mL of dimethyl sulphoxide at room temperature under nitrogen. The mixture is stirred for 1 hour, then mixed with 300 mL of saturated ammonium chloride solution and again stirred for 15 min. It is then diluted with 1.5 L of ether, the phases are separated, and the organic phase is washed 2× with saturated sodium chloride solution, dried over sodium sulphate and concentrated in vacuo. Yield: 9.5 g of the aldehyde.

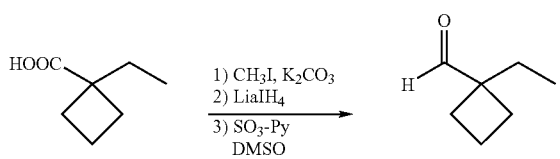

1f) Ethyl 4,4-(trimethylene)-2-hexenecarboxylate

A solution of 18.3 mL of triethyl phosphonoacetate in 20 mL of tetrahydrofuran is added dropwise to a suspension of 3.39 g of sodium hydride in 60 mL of tetrahydrofuran at 0° C. under nitrogen, and the mixture is stirred at room temperature for 30 min. The aldehyde (prepared in 1e) is then added dropwise to the reaction mixture at 0° C., and the mixture is stirred at room temperature for 3 hours. It is then quenched with saturated ammonium chloride solution and extracted 3× with ether, and the combined organic phases are washed 1× with water and 1× with saturated sodium chloride solution, dried over sodium sulphate and concentrated in vacuo. Chromatography on silica gel with hexane/ether (0-10%) results in 9.81 g of the ester.

$^1$H-NMR (CDCl$_3$): δ=0.71 (3H), 1.27 (3H), 1.65 (2H), 1.78-2.1 (6H), 4.18 (2H), 5.75 (1H), 6.97 (1H)

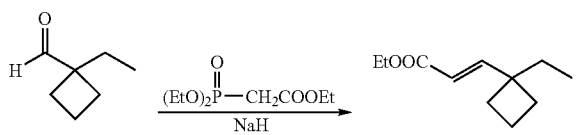

1g) 4,4-(Trimethylene)hexan-1-ol 78.5 mL of DIBAH are slowly added dropwise to a solution of 7.8 g of the ester prepared as in 1f) in 65 mL of methylene chloride at −70° C. under nitrogen. After 30 min, 20 mL of isopropanol and then 36 mL of water are slowly added dropwise to the reaction mixture. The mixture is stirred at room temperature for 2 hours, the precipitate is filtered off with suction and thoroughly washed with methylene chloride, and the filtrate is concentrated in vacuo. Chromatography on silica gel with hexane/ethyl acetate (0-40%) results in 5.4 g of the allyl alcohol.

5 Grams of the allyl alcohol are dissolved in 200 mL of ethyl acetate mixed with 500 mg of Pd/C and this is followed by filtration with suction through Cellite and thorough washing with ethyl acetate. Concentration of the filtrate in vacuo results in 4.5 g of the primary alcohol.

$^1$H-NMR (CDCl$_3$): δ=0.8 (3H), 1.2-1.9 (12H), 3.6 (2H)

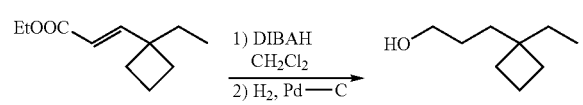

1h) 1-Phenylthio-4,4-(trimethylene)hexane

A solution of 6.19 g of p-toluenesulphonyl chloride in 7.4 mL of toluene is added dropwise to a mixture of 4.4 g of the alcohol prepared as in 1g), 25 mL of toluene, 997 mg of ammonium tetrabutyl bromide and 46 mL of 2N NaOH at 0° C. under nitrogen, and the mixture is stirred for 2 hours. The phases are then separated, and the organic phase is washed 3× with water and 1× with saturated sodium chloride solution, dried over sodium sulphate and concentrated in vacuo. Chromatography on silica gel with hexane/ether (0-20%) results in 4.6 g of the thioether.

$^1$H-NMR (CDCl$_3$): δ=0.75 (3), 1.39 (2H), 1.45-1.88 (10H), 2.88 (2H), 7.15-7.53 (5H)

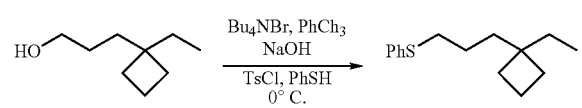

1i) 1-Phenylsulphonyl-4,4-(trimethylene)hexane

A solution of 18 g of ozone in 70 mL of water is added dropwise to a solution of 4.6 g of the product prepared as in 1 h) in 70 mL of methanol at 0-10° C. under nitrogen, and the mixture is stirred for 2 hours. It is then diluted with 100 mL of water and extracted 4× with ethyl acetate, and the combined organic phases are washed 1× with water, 2× with saturated thiosulphate solution and 1× with saturated sodium chloride solution, dried over sodium sulphate and concentrated in vacuo. Chromatography on silica gel with hexane/ethyl acetate (0-20%) results in 2.55 g of the sulphone.

$^1$H-NMR (CDCl$_3$): δ=0.7 (3H), 1.3-1.85 (12H), 3.08 (2H), 7.5-7.7 (3H), 7.9 (2H)

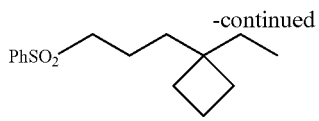
-continued

Synthesis Example 2

Methyl (5Z,13E)-(9R,11R)-9-chloro-11-hydroxy-17,17-tetramethylene-20-nor-5,13-prostadienoate 2.5 mg of pTsOH are added to a solution of 140 mg of the product prepared in Example 1 in 1.5 mL of methanol at 0° C. under nitrogen, and the mixture is stirred for 3 hours. The reaction mixture is then poured into 3 mL of saturated sodium carbonate solution and extracted 3× with ethyl acetate, and the combined organic phases are washed 1× with saturated sodium chloride solution, dried over sodium sulphate and concentrated in vacuo. Chromatography on silica gel with hexane/ethyl acetate (0-50%) results in 105 mg of the alcohol.

$^1$H-NMR (CDCl$_3$): δ=0.75 (3H), 1.38-2.4 (24H), 3.65 (3H), 3.9-4.13 (2H), 5.2-5.63 (4H)

Synthesis Example 3

(5Z,13E)-(9R,11R)-9-Chloro-11-hydroxy-17,17-tetramethylene-20-nor-5,13-prostadienoic acid 0.2 mL of 2N sodium hydroxide solution is added to a solution of 68 mg of the alcohol prepared in Example 2 in 1 mL of methanol under nitrogen, and the mixture is stirred for 5 hours. It is then diluted with 1 mL of water, adjusted to pH 3 with 2N hydrochloric acid and extracted 3× with ethyl acetate, and the combined organic phases are washed 1× with saturated sodium chloride solution, dried over sodium sulphate and concentrated in vacuo. Chromatography on silica gel with hexane/ethyl acetate (50-80%) results in 50.3 mg of the carboxylic acid.

$^1$H-NMR (CDCl$_3$): δ=0.75 (3H), 1.38-2.4 (24H), 3.9-4.1 (2H), 5.2-5.62 (4H)

Biological Example 1

Detection of the Antagonism of the Human Prostaglandin E$_2$ (Subtype EP$_2$) Receptor Signal 1.1. Principle of Detection The binding of PGE$_2$ to the EP$_2$ subtype of the human PGE$_2$ receptor induces activation of membrane-associated adenylate cyclases and leads to the formation of cAMP. In the presence of the phosphodiesterase inhibitor IBMX, cAMP which has accumulated due to this stimulation and been released by cell lysis is employed in a competitive detection method. In this assay, the cAMP in the lysate competes with cAMP-XL665 for binding of an Eu cryptate-labelled anti-cAMP antibody.

This results, in the absence of cellular cAMP, in a maximum signal which derives from coupling of this antibody to the cAMP-XL665 molecule. After excitation at 337 nm, this results in a FRET (fluorescence resonance energy transfer)-based, long-lived emission signal at 665 nm (and at 620 nm). The two signals are measured in a suitable measuring instrument with a time lag, i.e. after the background fluorescence has declined. Any increase in the low FRET signal caused by prostaglandin E$_2$ addition (measured as well ratio change=emission$_{665\ nm}$/emission$_{620\ nm}$*10 000) shows the effect of antagonists.

1.2. Detection Method 1.2.1. Antagonism Assay (Data for Each Well of a 384-Well Plate):

The substance solutions (0.75 μL) introduced into an assay plate and 30% DMSO are dissolved in 16 μL of a KRSB+ IBMX stimulation solution (1× Krebs-Ringer Bicarbonate Buffer; Sigma-Aldrich #K-4002; including 750 μM 3-isobutyl-1-methylxanthine Sigma-Aldrich #I-7018), and then 15 μL thereof are transferred into a media-free cell culture plate which has been washed with KRSB shortly beforehand.

After preincubation at room temperature (RT) for 30 minutes, 5 μL of a 4×PGE$_2$ solution (11 nM) are added, and incubation is carried out in the presence of the agonist at RT for a further 60 min (volume: ~20 μl) before the reaction is then stopped by adding 5 μL of lysis buffer and incubated at RT for a further 20 min (volume: ~25 μL). The cell lysate is then transferred into a measuring plate and measured in accordance with the manufacturer's information (cyclic AMP kit Cisbio International #62AMPPEC).

1.2.2. Agonism Assay (Data for Each Well of a 384-Well Plate):

The substance solutions (0.75 μL) introduced into an assay plate and 30% DMSO are dissolved in 16 μL of a KRSB+ IBMX stimulation solution (1× Krebs-Ringer Bicarbonate Buffer; Sigma-Aldrich #K4002; including 750 μM 3-isobutyl-1-methylxanthine Sigma-Aldrich #I-7018), and then 15 μL thereof are transferred into a media-free cell culture plate which has been washed with KRSB shortly beforehand.

After incubation at room temperature (RT; volume: ~15 μL) for 60 minutes, the reaction is then stopped by adding 5 μL of lysis buffer and incubated at RT for a further 20 min (volume: ~20 μL). The cell lysate is then transferred into a measuring plate and measured in accordance with the manufacturer's information (cyclic AMP kit Cisbio International #62AMPPEC).

The test compound showed in the cellular agonism assay a very high activity (EC$_{50}$<9.5×10e−5M) without any inhibition in the antagonism assay (IC$_{50}$>2×10e−5M).

Biological Example 2

The EP$_2$ Subtype of the PGE$_2$ Receptor and the Preovulatory Cumulus Expansion 2.1. Background:

In the preovulatory antral follicle, the oocyte is surrounded by cumulus cells which form a dense ring of cells around the oocyte. After the LH peak (lutenising hormone), a series of processes is activated and leads to a large morphological change in this ring of cells composed of cumulus cells. In this case, the cumulus cells form an extracellular matrix which leads to so-called cumulus expansion (Vanderhyden et al. Dev Biol. 1990 August; 140(2):307-317). This cumulus expansion is an important component of the ovulatory process and of the subsequent possibility of fertilisation.

Prostaglandins, and here prostaglandin E$_2$, whose synthesis is induced by the LH peak, are of crucial importance in cumulus expansion. Prostanoid EP$_2$ knockout mice (Hizaki et al. Proc Natl Acad Sci USA. 1999 Aug. 31; 96(18):10501-6.) show a markedly reduced cumulus expansion and severe subfertility, demonstrating the importance of the prostanoid EP$_2$ receptor for this process.

2.2. Cumulus Expansion Assay In Vitro

Folliculogenesis is induced in immature female mice (strain: CD1 (ICR) from Charles River) at an age of 20-24 days by a single dose (intraperitonal) of 7.5 I.U. of PMSG (Pregnant Mare Serum Gonadotropine; Sigma G-4877, Lot 68H0909). 47-50 hours after the injection, the ovaries are removed and the cumulus-oocyte complexes are removed. The cumulus complex is not yet expanded at this stage.

The cumulus-oocyte complexes are then incubated with prostaglandin $E_2$ ($PGE_2$) (1 µM), vehicle control (ethanol) or test substances for 20-24 hours. Medium: alpha-MEM medium with 0.1 mM IBMX, pyruvates (0.23 mM) glutamines (2 mM), pen/strep 100 IU/mL pen. and 100 µg/mL strep.) and HSA (8 mg/mL)). Cumulus expansion is then established through the division into four stages (according to Vanderhyden et al. Dev Biol. 1990 August; 140(2):307-317).

The test substance leads to a concentration-dependent great expansion in the cumulus complex. The cumulus expansion induced by the test substance is equivalent in concentrations of 0.5 µM and 1 µM to the cumulus expansion induced by the natural $EP_2$ receptor agonist $PGE_2$ in a concentration of 1 µM (n=16 cumulus-oocyte complexes per group; see FIG. 1).

2.3. Ovulation Assay In Vivo:

Folliculogenesis is induced in immature female mice (strain: (B6D2F1) from Charles River) at an age of 16-20 days by a single dose (intraperitonal) of 10 I.U. of PMSG (Pregnant Mare Serum Gonadotropine; Sigma G-4877, Lot 68H0909). 47-50 hours after the PMSG stimulation, a dose of 10 IU of HCG (human chorion gonadotropin) is used to induce final follicle maturation and ovulation. The test substance is administered 10 hours, 5 hours and 0 hours before the HCG dose (s.c. in benzyl benzoate/castor oil 1+4 v/v). Fourteen hours after the HCG dose, the autopsy is performed and the number of ovulated oocytes in the fallopian tube is determined.

The $EP_2$ agonist leads to a concentration-dependent significant increase in ovulated oocytes. This significant increase in ovulated oocytes occurs on administration of only 0.00015 mg/animal in each case and shows that it is possible to increase the number of ovulated oocytes even with a standard dose of HCG used for ovulation (n=11-12 animals per group; **$p<0.005$ and *$p<0.05$).

Biological Example 3

The $EP_2$ Subtype of the $PGE_2$ Receptor and the Cytokine Release Assay 3.1. Background Growing evidence suggests that endometriosis is associated with a significant inflammatory response that may be mediated by activated macrophages and lymphocytes and increased levels of cytokines, chemokines, and growth factors. These inflammatory processes have been hypothesized to mediate some of the clinical features associated with endometriosis. The peritoneal fluid of women with endometriosis is known to contain more inflammatory cells and their associated cytokines, chemokines, and growth factors. (Murphy A A. Clinical aspects of endometriosis. Ann NY Acad Sci. March 2002; 955:1-10). The result is an environment that promotes implantation and proliferation.

Prostaglandins, and here prostaglandin $E_2$, reduces the expression of inflammatory cytokines, such as TNFα from activated macrophages. Prostanoid $EP_2$ knockout mice (Shinomiya S et al., Bioch Phar 2001; 61 1153) fail to respond to $EP_2$ agonists, demonstrating the importance of the prostanoid $EP_2$ receptor for this process.

3.2. Cytokine Release Assay In Vitro

Human donor monocyte-derived dendritic cells are cultured in RPMI-1640 containing 10% fetal bovine serum for six days in the presence of 10 ng/mL IL-4 and 200 ng/mL GM-CSF. The cells are activated with various activation stimuli: 10 ng/mL LPS (Sigma), 5 µg/mL recombinant human CD-40 ligand (R&D Systems), or 5 µM Human CpG-DNA (HyCult Biotechnology) in the presence of prostaglandin $E_2$ ($PGE_2$) (1 µM), vehicle control (DMSO) or test substances (1 µM) for 18 hours. The levels of cell culture supernatant TNFα for individual donors is measured by commercial ELISA kits. The test substances lead to an inhibition in the cytokine levels measured in the culture supernatant as shown in Table 1.

3.3. Cytokine Release Assay Ex Vivo

The test substance or vehicle control is administered intraperitoneally to treatment groups of CD-1 mice weighing 30-35 grams each (n=5). Twenty minutes later the mice are euthanized, spleens removed and splenocytes are cultured in RPMI+10% fetal bovine serum. Cells are activated with PHA and ConA in the absence of test substance and cultured for 18 hours. The levels of cell culture supernatant TNFα for individual mice are measured by commercial ELISA kits. The $EP_2$ agonist causes a significant decrease in TNFα as shown in FIG. 3.

Biological Example 4

Demonstration of Inhibition of T Lymphocyte Th-1 Cytokine Release 4.1. Principle The activation of a human T lymphocyte by an antigen presenting cell and antigen through the T cell receptor is mimicked in experimental conditions by the lectin Concanavilin A (ConA). It is known that ConA binds to the T cell receptor and stimulates the cell to release various cytokines. One of the Th-1 released cytokines is INF-γ. The biochemistry and biological activities of INF-γ have been extensively reviewed.

4.2. Detection Method

INF-γ is a dimer of the expressed 143 amino acid protein. Enzyme linked immuno sorbant assays (ELISA) based on antibodies specific to INF-γ are commercially available. Standards and samples are pipetted into the wells of a microplate. An antibody specific to human INF-γ is added to the wells. A substrate is added to the wells and color develops in proportion to the amount of INF-γ bound. The intensity of the color is measured.

4.3. Procedure

Peripheral blood lymphocytes are isolated from human donors using a Ficoll density gradient and residual erythrocytes removed by selective lysis. The lymphocytes are cultured at approximately $10^6$ cells per ml in RPMI1640 with 10% additional fetal bovine serum. The cell cultures are activated with 2 µg/ml of ConA as described above. Test sub stance is added at various dilutions during the ConA activation. Cells are incubated for approximately 18 hr at 37 C. INF-γ released during activation is measured by ELISA.

Biological Example

Demonstration of Inhibition of Human Monocyte Derived Dendritic Cell Cytokine Release 5.1. Principle:

Dendritic cells (DC) are the most potent antigen presenting cells and play a central role in the immune response. Following stimulation through the toll-like receptors (TLR) DCs express and release proinflammatory cytokines and chemokines and may induce activation and proliferation of naïve T cells. The binding of an $EP_2$ agonist to the DC EP receptor inhibits TLR4 ligand (LPS) stimulated Interleukin 12 (IL-12) release. The binding of an $EP_2$ agonist to the DC EP receptor does not inhibit TLR4 ligand (LPS) stimulated Interleukin 10 (IL-10) release. Therefore an $EP_2$ agonist skews the CD4 T cell differentiation away from the Th-lineage.

5.2. Detection Method

IL-12 is a 75 kDa glycoprotein heterodimer (p70) composed of two genetically unrelated subunits linked by a disulfide bond. Enzyme linked immuno sorbant assays (ELISA) based on antibodies specific to IL-12 p70 are commercially available. Standards and samples are pipetted into the wells of a microplate. An antibody specific to human IL-12 is added to the wells. A substrate is added to the wells and color develops in proportion to the amount of IL-12 bound. The intensity of the color is measured.

IL-10 initially designated cytokine synthesis inhibitory factor (CSIF), was originally identified as a product of Th-2 clones that suppressed the production of cytokines by Th-1 clones responding to stimulation by antigen in the presence of antigen-presenting cells. IL-10 is a dimer composed of two identical 160 amino acid subunits. Enzyme linked immuno sorbant assays (ELISA) based on antibodies specific to IL-10 are commercially available. Standards and samples are pipetted into the wells of a microplate. An antibody specific to human IL-10 is added to the wells. A substrate is added to the wells and color develops in proportion to the amount of IL-10 bound. The intensity of the color is measured.

5.3. Procedure

Human monocyte derived dendritic cells are isolated from human donors using a Ficoll density gradient and residual erythrocytes removed by selective lysis. CD14 MicroBeads are used for separation of human cells based on the expression of the CD14 antigen. The dendritic cells are cultured at approximately $1.5 \times 10^6$ cells per ml in RPMI 1640 with fetal bovine serum, 200 ng/ml GM-CSF (Leukine) and 10 ng/ml IL-4. The cells grow for a period of 3 days and then the media is changed. 10 ng/ml LPS is used to activate the cells. 1 µM of substance ($EP_2$ agonist) and 1 µM of $PGE_2$ are added during the LPS stimulation. Cells are incubated for approximately 18 hr at 37 C. IL-12 and Il-10 released during activation is measured by ELISA.

What is claimed is:
1. A compound of formula I

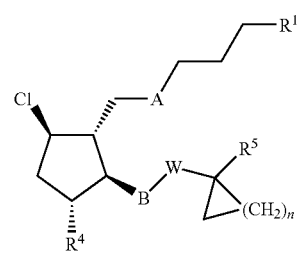

where
$R^1$ is $CH_2OH$, —$COOR^2$, —$CONHR^2$ or —$CONHR^3$;
$R^2$ is hydrogen, linear or branched $C_1$-$C_{10}$-alkyl which is optionally mono- to polyunsaturated and optionally mono- to polysubstituted by halogen, $C_1$-$C_4$-alkoxy, substituted $C_3$-$C_{10}$-aryl, optionally substituted $C_3$-$C_{10}$-aroyl, optionally substituted di-$C_1$-$C_5$-alkylamino, or tri- $C_1$-$C_5$-alkylamino, $C_3$-$C_{10}$-cycloalkyl which is optionally substituted by $C_1$-$C_4$-alkyl, $C_3$-$C_{10}$-aryl which is optionally substituted by phenyl, 1-naphthyl, 2-naphthyl which in turn is optionally substituted in position 3 and in position 4 by fluorine, chlorine, alkoxy or trifluoromethyl or in position 4 by hydroxy, halogen, phenyl, one or more $C_1$-$C_4$-alkyl groups, chloromethyl, fluoromethyl, trifluoromethyl, carboxy, hydroxy or $C_1$-$C_4$-alkoxy, or $C_3$-$C_7$-heterocycloalkyl;
$R^3$ is $C_1$-$C_{15}$-carboxylic acid or $C_1$-$C_{15}$-sulphonic acid;
A is cis-CH=CH— or —$CH_2$—$CH_2$—;
B is trans-CH=CH— or —$CH_2$—$CH_2$—;
W is $C_2$-$C_6$-alkylene;
$R^4$ is hydroxy, —O—$R^6$ or —O—$R^7$
$R^6$ is tetrahydropyranyl, tetrahydrofuranyl, trimethylsilyl, tert-butyldimethylsilyl, tert-butyldiphenylsilyl or tribenzylsilyl;
$R_7$ is $C_1$-$C_{15}$-carboxylic acid;
$R^5$ is hydrogen, $C_1$-$C_{10}$-alkyl or $C_1$-$C_{10}$-alkenyl; and
n is the number 1-4; or
a salt thereof or a cyclodextrin clathrate thereof with a physiologically tolerated base.

2. A compound according to claim 1, where
$R^1$ is $CH_2OH$, —$COOR^2$, —$CONHR^2$ or —$CONHR^3$;
$R^2$ is hydrogen, linear or branched $C_1$-$C_{10}$-alkyl which is optionally mono- to polyunsaturated and optionally monosubstituted by fluorine, chlorine, bromine, $C_1$-$C_4$-alkoxy, $C_3$-$C_{10}$-aryl, $C_3$-$C_{10}$-aroyl, di-$C_1$-$C_5$-alkylamino, or tri- $C_1$-$C_5$-alkylamino, $C_5$-$C_6$-cycloalkyl which is optionally substituted by $C_1$-$C_4$-alkyl, $C_3$-$C_{10}$-aryl which is optionally substituted by phenyl which is optionally substituted in position 3 or 4 by fluorine, chlorine, alkoxy or trifluoromethyl or in position 4 by hydroxyl, or $C_5$-$C_6$-heterocycloalkyl which is interrupted one or more times by nitrogen, oxygen or sulphur;
$R^3$ is $C_1$-$C_{10}$-carboxylic acid or $C_1$-$C_{10}$-sulphonic acid;
A is cis-CH=CH— or —$CH_2$—$CH_2$—;
B is trans-CH=CH— or —$CH_2$—$CH_2$—;
W is $C_2$-$C_6$-alkylene;
$R^4$ is hydroxy;
$R^5$ is hydrogen, $C_1$-$C_6$-alkyl or $C_1$-$C_{10}$-alkenyl; and
n is the number 1-4.

3. A compound according to claim 1, where
R$^1$ is CH$_2$OH, —COOR$^2$, —CONHR$^2$ or —CONHR$^3$;
R$^2$ is hydrogen, C$_1$-C$_4$-alkyl which is optionally substituted by phenyl, C$_5$-C$_6$-cycloalkyl, or C$_3$-C$_6$-aryl which is optionally substituted by phenyl;
R$^3$ is C$_1$-C$_6$-carboxylic acid or a C$_1$-C$_6$-sulphonic acid;
A is cis-CH=CH— or —CH$_2$—CH$_2$—;
B is trans-CH=CH— or —CH$_2$—CH$_2$—;
W is C$_2$-alkylene;
R$^4$ is hydroxy;
R$^5$ is hydrogen, saturated C$_1$-C$_4$-alkyl or C$_1$-C$_5$-alkenyl; and
n is the number 1-4.

4. A pharmaceutical composition comprising of at least one compound according to claim 1.

5. A pharmaceutical composition according to claim 4, further comprising one or more suitable formulating substances and/or carriers.

6. A pharmaceutical composition according to claim 4, wherein said composition is in a form suitable for enteral, parenteral, vaginal or oral administration.

7. A method of reducing the release of Th-1 cytokines in a patient comprising administering to said patient an effective amount of a compound according to claim 1.

8. A method of promoting fertility in a patient comprising administering to said patient an effective amount of a compound according to claim 1.

9. A method of promoting in vitro fertilization in a patient comprising administering to said patient an effective amount of a compound according to claim 1.

10. A method of promoting ovulation in a patient comprising administering to said patient an effective amount of a compound according to claim 1.

11. A method of inducing cumulus expansion in a patient comprising administering to said patient an effective amount of a compound according to claim 1.

12. A method of reducing elevated intraocular pressure in a patient comprising administering to said patient an effective amount of a compound according to claim 1.

13. A process for preparing a compound according to claim 1, said process comprising:
reacting an aldehyde of formula II with a carbanion of a sulphone of formula III

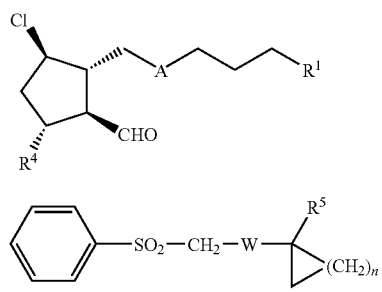

wherein R$_1$ is —COOR$_2$ or —CONHR$_3$, and where the free OH group in R$^4$ is protected;
acetylating the resulting hydroxysulphone;
subjecting the resultant compound to reductive elimination to give the resulting olefin;
and, where appropriate;
deprotecting hydroxy groups which are protected in any sequence;
and, where appropriate,
esterifying, etherifying, and/or hydrogenating double bonds and/or esterifying an esterified carboxy group and/or a free carboxy group and/or converting a free carboxy group into an amide and/or reducing a free or esterified carboxy group.

14. A compound according to claim 1, wherein R$^2$ is hydrogen,
linear or branched C$_1$-C$_{10}$-alkyl which is optionally mono- to polyunsaturated and optionally mono- to polysubstituted by halogen, C$_1$-C$_4$-alkoxy, C$_3$-C$_{10}$-aryl substituted by halogen, phenyl, C$_1$-C$_4$-alkyl, chloromethyl, fluoromethyl, trifluoromethyl, carboxy, hydroxy or C$_1$-C$_4$-alkoxy, C$_3$-C$_{10}$-aroyl which is optionally substituted by halogen, phenyl, C$_1$-C$_4$-alkyl, chloromethyl, fluoromethyl, trifluoromethyl, carboxy, hydroxy or C$_1$-C$_4$-alkoxy, di-C$_1$-C$_5$-alkylamino which is optionally substituted by halogen, methoxy, ethoxy, phenyl, dimethylamino, diethylamino, or dimethylaminopropyl, or tri- C$_1$-C$_5$-alkylamino,
C$_3$-C$_{10}$-cycloalkyl which is optionally substituted by C$_1$-C$_4$-alkyl,
C$_3$-C$_{10}$-aryl which is optionally substituted by phenyl, 1-naphthyl, 2-naphthyl which in turn is optionally substituted in position 3 and in position 4 by fluorine, chlorine, alkoxy or trifluoromethyl or in position 4 by hydroxy, halogen, phenyl, one or more C$_1$-C$_4$-alkyl groups, chloromethyl, fluoromethyl, trifluoromethyl, carboxy, hydroxy or C$_1$-C$_4$-alkoxy, or
C$_3$-C$_7$-heterocycloalkyl.

15. A compound according to claim 2, wherein before R$^2$ is hydrogen,
linear or branched C$_1$-C$_{10}$-alkyl which is optionally mono- to polyunsaturated and optionally monosubstituted by fluorine, chlorine, bromine, C$_1$-C$_4$-alkoxy, C$_3$-C$_{10}$-aryl substituted by halogen, phenyl, C$_1$-C$_4$-alkyl, chloromethyl, fluoromethyl, trifluoromethyl, carboxy, hydroxy or C$_1$-C$_4$-alkoxy, C$_3$-C$_{10}$-aroyl which is optionally substituted by halogen, phenyl, C$_1$-C$_4$-alkyl, chloromethyl, fluoromethyl, trifluoromethyl, carboxy, hydroxy or C$_1$-C$_4$-alkoxy, di-C$_1$-C$_5$-alkylamino which is optionally substituted by halogen, methoxy, ethoxy, phenyl, dimethylamino, diethylamino, or dimethylaminopropyl, or tri- C$_1$-C$_5$-alkylamino,
C$_5$-C$_6$-cycloalkyl which is optionally substituted by C$_1$-C$_4$-alkyl,
C$_3$-C$_{10}$-aryl which is optionally substituted by phenyl which is optionally substituted in position 3 or 4 by fluorine, chlorine, alkoxy or trifluoromethyl or in position 4 by hydroxyl, or
C$_5$-C$_6$-heterocycloalkyl which is interrupted one or more times by nitrogen, oxygen or sulphur.

16. A compound according to claim 1, wherein before R$^2$ is methyl, ethyl, propyl, butyl, isobutyl, tert-butyl, pentyl, neopentyl, hexyl, heptyl, octyl, decyl, butenyl, isobutenyl, propenyl, pentenyl, benzyl, m-chlorobenzyl or p-chlorobenzyl.

17. A compound according to claim 2, wherein n is 2-3.

18. A compound according to claim 15, wherein n is 2-3.

19. A compound according to claim 3, wherein n is 2-3.

20. A compound according to claim 3, wherein n is 2.

21. A compound according to claim 1, wherein said compound is methyl (5Z,13E)-(9R,11R)-9-chloro-11-[(2H)-tetrahydropyran-2-yloxy]-17,17-tetramethylene-20-nor-5,13-prostadienoate.

22. A compound according to claim 1, wherein said compound is methyl (5Z,13E)-(9R,11R)-9-chloro-11-hydroxy-17,17-tetramethylene-20-nor-5,13-prostadienoate.

23. A compound according to claim 1, wherein said compound is (5Z,13E)-(9R,11R)-9-Chloro-11-hydroxy-17,17-tetramethylene-20-nor-5,13-prostadienoic acid.

* * * * *

UNITED STATES PATENT AND TRADEMARK OFFICE
CERTIFICATE OF CORRECTION

PATENT NO. : 7,563,924 B2
APPLICATION NO. : 11/602690
DATED : July 21, 2009
INVENTOR(S) : Buchmann et al.

It is certified that error appears in the above-identified patent and that said Letters Patent is hereby corrected as shown below:

Column 27, line 56 reads "wherein $R_1$ is -COOR$_2$ or -CONHR$_3$, and where the" should read -- wherein $R^1$ is -COOR$^2$ or -CONHR$^3$, and where the --.

Column 28, line 27 reads "A compound according to claim 2, wherein before $R^2$ is" should read -- A compound according to claim 2, wherein $R^2$ is --.

Column 28, line 48 reads "A compound according to claim 1, wherein before $R^2$ is" should read -- A compound according to claim 1, wherein $R^2$ is --.

Signed and Sealed this

Sixteenth Day of March, 2010

David J. Kappos
*Director of the United States Patent and Trademark Office*